United States Patent [19]
Brinker et al.

[11] Patent Number: 5,983,515
[45] Date of Patent: Nov. 16, 1999

[54] APPARATUS FOR MEASURING HEIGHTS IN DISSOLUTION TESTING EQUIPMENT

[75] Inventors: Gerald Brinker, North Brunswick; Thomas Hauck, Somerset, both of N.J.

[73] Assignee: Distek, Inc., North Brunswick, N.J.

[21] Appl. No.: 08/903,558

[22] Filed: Jul. 31, 1997

Related U.S. Application Data

[60] Provisional application No. 60/023,103, Aug. 1, 1996.

[51] Int. Cl.⁶ ........................................ G01B 5/14
[52] U.S. Cl. ................................. 33/810; 33/542
[58] Field of Search ..................... 33/542, 542.1, 33/810, 783, 806, 809, 811, 812, 832, 833, 834

[56] References Cited

U.S. PATENT DOCUMENTS

| | | | |
|---|---|---|---|
| 1,262,678 | 4/1918 | Lapoint | 33/812 |
| 4,279,860 | 7/1981 | Smolen . | |
| 4,335,438 | 6/1982 | Smolen . | |
| 4,897,931 | 2/1990 | Goulette | 33/810 |
| 5,589,649 | 12/1996 | Brinker et al. . | |

OTHER PUBLICATIONS

"Pharmacopeia", USP XXII, U.S. Pharmacopeial Convention, Inc., 12601 Twinbrook Parkway, Rockville, MD 20852, pp. xlii and 1578–1579, Jan. 1, 1990.

*Primary Examiner*—Christopher W. Fulton
*Attorney, Agent, or Firm*—T. Daniel Christenbury

[57] ABSTRACT

An apparatus for use with a dissolution testing device comprising a vessel and a shaft with a stir element affixed to one end thereof for placement within the vessel. In one embodiment, the apparatus has a front portion having a first jaw portion and a back portion having a second jaw portion. The front portion is slidably coupled to the front portion, and the first and second jaw portions form a jaw interposable between the bottom of the stir element and the inside bottom of the vessel. The jaw has a jaw distance corresponding to the position of the front portion relative to the back portion. The apparatus also includes a shaft alignment portion for aligning the apparatus parallel to the shaft, and a measurement portion for providing a distance reading corresponding to the gauge jaw distance.

6 Claims, 2 Drawing Sheets

APPARATUS FOR MEASURING HEIGHTS IN DISSOLUTION TESTING EQUIPMENT

CROSS-REFERENCES TO RELATED APPLICATIONS

This non-provisional U.S. national application, filed under 35 U.S.C. § 111(a), claims, under 35 U.S.C. § 119(e)(1), the benefit of the filing date of provisional U.S. national application Ser. No. 60/023,103, filed under 25 U.S.C. § 111(b) on Aug. 1, 1996, the entirety of which is incorporated herein by reference.

BACKGROUND OF THE INVENTION

1. Field of the Invention

The present invention relates to the field of dissolution testing and, in particular, to apparatuses for measuring heights in dissolution testing equipment.

2. Description of the Related Art

Dissolution testing and apparatuses for performing such are known in the art. U.S. Pat. Nos. 4,279,860 (Smolen) and 4,335,438 (Smolen) provide descriptions of the art of dissolution testing. In general, dissolution testing is used to determine the rate of dissolution of a material in a solution, such as dissolution testing of pharmaceuticals in solid, semi-solid, or transdermal dosage form. For example, dissolution testing may be used to determine the rate of dissolution of pharmaceuticals in dosage form in specific test solutions to simulate digestion in a human. The requirements for such dissolution testing apparatuses are provided in United States Pharmacopeia (USP), Edition XXII, Section 711, Dissolution (1990). A dissolution testing apparatus is described in U.S. Pat. No. 5,589,649, issued Dec. 31, 1996 to Brinker, the entirety of which is incorporated herein by reference.

Conventional dissolution testing devices have one or more test vessels in which test solutions may be placed. One conventional configuration of a dissolution testing apparatus has, for each test vessel, a basket-type stirring element consisting of a metal shaft with a cylindrical basket at the lower end thereof. After placing the dosage to be dissolved into the basket, the stirring element is lowered into the test solution near the center of the vessel and rotated at a specified rate (typically measured in revolutions per minute (RPM)) for a specified duration. Samples of the test solutions may be periodically withdrawn from the vessels to determine the degree of dissolution of the dosages as a function of time.

Another conventional configuration of a dissolution testing apparatus has a paddle-type stirring element consisting of a metal shaft with a metal blade at the end. In dissolution testing with this type of apparatus, the stirring element is rotated within the test solution with the dosage at the bottom of the vessel. In either conventional configuration, a vessel is utilized, along with a shaft having either a paddle or a basket at the bottom end thereof. In the present application, the term "stir element" may be used as a general term to refer either to a paddle or basket affixed to the bottom end of a shaft placeable within a dissolution testing vessel.

When inserting the shaft with stir element into the vessel, it is important to ensure that there is a precise, specified distance, or height, between the bottom of the stir element and the inside bottom of the vessel. In the present application, the distance between the bottom of the stir element and the inside bottom of the vessel may be referred to as the stir element height or simply height. This height is an important variable that can significantly affect the results of a dissolution test. Incorrect distances between paddle or basket and the bottom of the vessel can alter the fluid hydrodynamics and distort dissolution rates. The USP procedure for dissolution testing provides: "The distance of 25±2 mm between the [paddle] blade [or basket] and the inside bottom of the vessel is maintained during the test."

Existing devices enable the setup of this distance in each vessel, but cannot quantify or verify the accuracy of this critical parameter. There is a need, therefore, for a means for ensuring that there is a precise, specified distance between the bottom of the stir element and the inside bottom of the vessel.

Further objects and advantages of this invention will become apparent from the detailed description of a preferred embodiment which follows.

SUMMARY

An apparatus for use with a dissolution testing device comprising a vessel and a shaft with a stir element affixed to one end thereof for placement within the vessel. In one embodiment, the apparatus has a front portion having a first jaw portion and a back portion having a second jaw portion. The front portion is slidably coupled to the back portion, and the first and second jaw portions form a jaw interposable between the bottom of the stir element and the inside bottom of the vessel. The jaw has a jaw distance corresponding to the position of the front portion relative to the back portion. The apparatus also includes a shaft alignment portion for aligning the apparatus parallel to the shaft, and a measurement portion for providing a distance reading corresponding to the gauge jaw distance.

BRIEF DESCRIPTION OF THE DRAWINGS

These and other features, aspects, and advantages of the present invention will become more fully apparent from the following description, appended claims, and accompanying drawings in which:

DESCRIPTION OF THE PREFERRED EMBODIMENT

Figure 1:
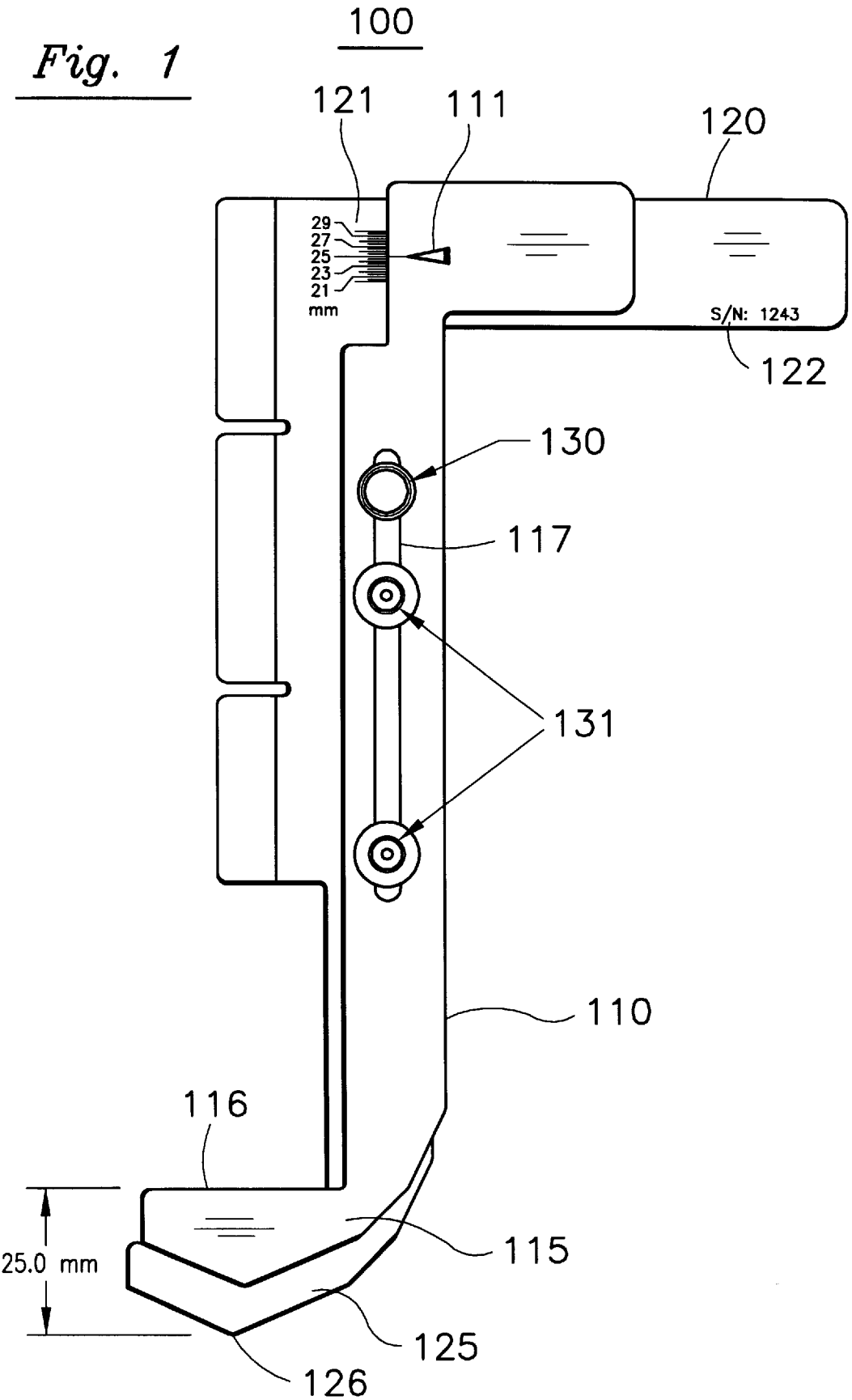
FIG. 1 is a perspective view of a gauge for measuring heights in dissolution testing equipment, in accordance with an embodiment of the present invention.

Referring now to FIG. 1, there is shown a perspective view of a gauge 100 for measuring heights in dissolution testing equipment, in accordance with an embodiment of the present invention. Gauge 100 comprises a front portion 110 and back portion 120, which are coupled together by guide screws 131 and locking thumbscrew 130. Front portion 110 and back portion 120 are preferably composed of a rigid metal, such as stainless steel, and a relatively flat, having a preferred thickness of ⅛ inch. Front portion 110 has a jaw portion 115, which has a top jaw surface 116. Front portion 110 further comprises a channel 117 and precision scale pointer 111.

Figure 2:
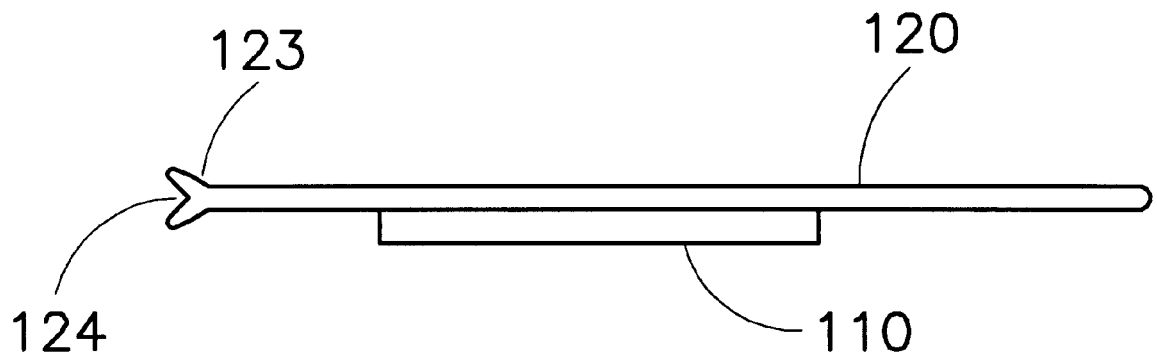
FIG. 2 is a plan view of a gauge for measuring heights in dissolution testing equipment, in accordance with an embodiment of the present invention.

Back portion 120 comprises serial number 122 etched into the top end thereof, precision scale marks 121, and jaw portion 125, which has a bottom jaw surface 126. Back portion 120 further comprises three angled tabs 123, each of which has a "V" cross section 124 (as shown in FIG. 2) for precision placement of gauge 100 against a shaft of a dissolution testing apparatus, where the shaft has a stir element (i.e. basket or paddle) affixed to the lower end thereof, and where the shaft and stir element are for placement within a vessel of the dissolution testing apparatus.

Front portion 110 and back portion 120 may be slid up and down relative to one another, along the direction of channel 117, within the limits placed by guide screws 131 within channel 117. Gauge 100 is designed and calibrated so that there are exactly 25 mm between top jaw surface 116 and bottom jaw surface 126 when scale pointer 111 matches up against the "25 mm" line of scale marks 121. This distance may be referred to herein as the gauge jaw distance. At this 25 mm point, guide screws 131 are preferably approximately at the center of the permitted travel distance within channel 117.

In one embodiment, the gauge jaw distance is adjustable between 21 and 29 mm, which corresponds to the limits of travel of front portion 110 relative to back portion 120 and to scale marks 121. Thus, when front portion 110 is lowered as far as possible (relative to back portion 120), the gauge jaw distance is 21 mm and scale pointer 111 points to the scale mark for 21 mm. Similarly, when front portion 110 is raised as far as possible, the gauge jaw distance is 29 mm and scale pointer 111 points to the scale mark for 29 mm.

As will be appreciated, locking thumbscrew 130, when tightened, prevents vertical movement along channel 117, and thus allows front portion 110 to be locked at its current position relative to back portion 120. Thus, thumbscrew 130 may be used to fix the gauge jaw distance of gauge 100. In one embodiment, thumbscrew 130 is a knurled locking thumbscrew, and is able to lock the gauge with a precision of within ±0.5 mm. Angled tabs 123 are preferably employed to place gauge 100 precisely in alinement with the testing apparatus shaft, and also allows for easy removal of the gauge without disturbing the current adjustment or height of the shaft within a vessel.

Height Setting

As will be appreciated, gauge 100 may be used either to accurately and precisely adjust the stir element height prior to a dissolution test, or to verify or measure the stir element height of a stir element already placed within a vessel. In order to adjust the height of a given stir element in a given vessel to a preselected height within the range of gauge 100, for example to 25 mm, locking thumbscrew 130 is loosened slightly, and front portion 110 is slid relative to back portion 120 until scale pointer 111 points exactly to the 25 mm scale line 121. Then, locking thumbscrew 130 is tightened to lock the gauge jaw distance at 25 mm.

Next, gauge 100 is placed into position under the stir element, and angled tabs 123 are positioned against the shaft. As will be appreciated, this precisely aligns gauge 100 parallel to the center axis of the shaft. At this point, jaws 115 and 125 will be vertically between the bottom of the stir element and the inside bottom of the vessel. The shaft is gently lowered (to avoid breaking a glass vessel, for example) until top jaw surface 116 touches the bottom of the stir element and bottom jaw surface 126 touches the inside bottom of the vessel. At this point, the stir element height is precisely 25 mm, and the shaft and stir element may be locked into place with a collar or other suitable device. Gauge 100 is then carefully manipulated (e.g., by rotation and tilting) to remove it from the vessel, without disturbing the shaft or its vertical placement or setting within the vessel. As will be appreciated, V-shaped angled tabs 123 facilitate the easy removal of gauge 100 without disturbing the shaft adjustment.

Height Measuring

If a shaft and stir element are already fixedly placed within a vessel, it may be desirable to measure the stir element height to ensure that it is acceptable. In order to measure the height of a given stir element in a given vessel, locking thumbscrew 130 is loosened slightly, and front portion 110 is slid relative to back portion 120 to achieve the minimum gauge jaw distance, e.g. until scale pointer 111 points to the 21 mm scale line 121. As will be appreciated, minimizing the gauge jaw distance facilitates moving gauge 100 into measuring position relative to the shaft and vessel.

Next, gauge 100 is placed into position under the stir element, with bottom jaw surface 126 placed against the inside bottom of the vessel. Angled tabs 123 are positioned against the shaft, to precisely align gauge 100 parallel to the center axis of the shaft. Using one hand to hold back portion 120 down so that bottom jaw surface 126 stays in contact with the inside bottom of the vessel, front portion 110 is slid upwards, until top jaw surface 116 touches the bottom of the stir element.

At this point, the gauge jaw distance, and the corresponding scale line 121 pointed to by scale pointer 111, are equal to the stir element height. Thus, the stir element height may be read directly from scale pointer 111 and scale lines 121. Further, if desired, locking screw 130 may be tightened at this point to lock in the reading indicated by scale pointer 111 and scale lines 121. Gauge 100 may then be rotated and tilted to remove it from the vessel, without disturbing the shaft or its vertical placement or setting within the vessel. If the measured height deviates too much from the desired height—e.g., if the measured height is not between 23 and 27 mm—then the height adjustment may be determined to be in error.

Thus, as will be appreciated, gauge 100 comprises front and back portions 110 and 120, which are slidably coupled to one another. Gauge 100 comprises a jaw means (e.g., jaws 115, 125) able to be interposed between the bottom of a stir element at the end of a shaft placed within a vessel, and the inside bottom of the vessel; the jaw means having a gauge jaw distance that varies as the front and back portions are slid against one another. Gauge 100 also comprises shaft alignment means (e.g., angled tabs 123), preferably formed from or affixed to back portion 120, which are used to precisely align gauge 100 parallel to the center axis of the shaft. Gauge 100 further comprises scale or measurement means (e.g., scale lines 121 and scale pointer 111) that provide a measurement or distance reading corresponding to the gauge jaw distance. Gauge 100 also comprises locking means (e.g., locking thumbscrew 130) for securing front portion 110 to back portion 120 by preventing relative sliding.

In one embodiment, scale lines 121, scale pointer 111, and serial number 122 are permanently etched on the face of gauge 100, as illustrated, to help reduce label tampering or instrument drift.

It will be understood that various changes in the details, materials, and arrangements of the parts which have been described and illustrated above in order to explain the nature of this invention may be made by those skilled in the art without departing from the principle and scope of the invention as recited in the following claims.

What is claimed is:

1. An apparatus for use with a dissolution testing device comprising a vessel and a shaft with a stir element affixed to one end thereof for placement within the vessel, the apparatus comprising:

(a) a front portion having a first jaw portion;

(b) a back portion having a second jaw portion, wherein:
the front portion is slidably coupled to the back portion;
the first and second jaw portions form a jaw means; and
the jaw means has a jaw distance corresponding to the position of the front portion relative to the back portion;

(c) a shaft alignment portion having a plurality of angled tabs; and (d) a measurement means for providing a distance reading corresponding to the gauge jaw distance.

2. The apparatus of claim 1, wherein, the front portion comprises a sliding channel, the apparatus further comprising two guide screws coupled to the back portion and slidably positioned within the sliding channel.

3. The apparatus of claim 2, further comprising a locking screw coupled to the back portion and slidably positioned within the sliding channel for securing the front portion to the back portion.

4. The apparatus of claim 1, wherein the first jaw portion comprises a top jaw surface for contacting the bottom of the stir element and the second jaw portion comprises a bottom jaw surface for contacting the inside bottom of the vessel.

5. The apparatus of claim 1, wherein the measurement means comprises a plurality of scale lines etched onto the back portion and a scale pointer etched onto the front portion, wherein the scale pointer aligns with a scale line corresponding to the gauge jaw distance.

6. The apparatus of claim 1, wherein said plurality of angled tabs is three angled tabs.

* * * * *